US012635852B2

(12) United States Patent　　　　　(10) Patent No.:　US 12,635,852 B2
Thuemen　　　　　　　　　　　　　　　(45) Date of Patent:　　May 26, 2026

(54) ENDOSCOPE

(71) Applicant: OLYMPUS Winter & Ibe GmbH, Hamburg (DE)

(72) Inventor: Alrun Thuemen, Hamburg (DE)

(73) Assignee: OLYMPUS Winter & Ibe GmbH, Hamburg (DE)

( * ) Notice: Subject to any disclaimer, the term of this patent is extended or adjusted under 35 U.S.C. 154(b) by 204 days.

(21) Appl. No.: 18/385,524

(22) Filed: Oct. 31, 2023

(65) Prior Publication Data

US 2024/0138654 A1　　May 2, 2024

Related U.S. Application Data

(60) Provisional application No. 63/421,653, filed on Nov. 2, 2022.

(51) Int. Cl.
　　*A61B 1/00*　　　　　(2006.01)
　　*A61B 1/07*　　　　　(2006.01)
(52) U.S. Cl.
　　CPC ...... *A61B 1/00119* (2013.01); *A61B 1/00066* (2013.01); *A61B 1/00114* (2013.01); *A61B 1/07* (2013.01); *A61B 1/0011* (2013.01)
(58) Field of Classification Search
　　CPC ............ A61B 1/00066; A61B 1/00114; A61B 1/00119; A61B 1/07
　　See application file for complete search history.

(56) References Cited

U.S. PATENT DOCUMENTS

| | | | | |
|---|---|---|---|---|
| 5,810,620 | A | * | 9/1998 | Kobayashi ......... A61B 1/00128 |
| | | | | 439/607.17 |
| 2015/0150441 | A1 | * | 6/2015 | Ouyang ................. A61B 1/015 |
| | | | | 600/109 |
| 2017/0188795 | A1 | * | 7/2017 | Ouyang ................. A61B 1/015 |
| 2021/0290044 | A1 | * | 9/2021 | Thuemen ........... A61B 1/00124 |
| 2021/0330176 | A1 | | 10/2021 | Thuemen et al. |
| 2022/0280030 | A1 | | 9/2022 | Thuemen et al. |

FOREIGN PATENT DOCUMENTS

| | | |
|---|---|---|
| DE | 10 2019 100 395 A1 | 7/2020 |
| DE | 10 2021 105 244 B3 | 6/2022 |
| DE | 20 2022 103 092 U1 | 6/2022 |
| JP | S58190422 A | 11/1983 |

OTHER PUBLICATIONS

German Search Report dated Jul. 24, 2023 received in 10 2022 129 052.2.
Japanese Office Action dated Dec. 26, 2025 received in 2023-186927.

* cited by examiner

*Primary Examiner* — Aaron B Fairchild
(74) *Attorney, Agent, or Firm* — Scully, Scott, Murphy & Presser, P.C.

(57)　　　　　　ABSTRACT

An endoscope including: a shaft assembly; and a handle assembly. The shaft assembly includes: a fiber tube; an outer shaft tube arranged around the fiber tube; and a support proximally extending from the outer shaft tube. The handle assembly is arranged around the support, and an electrical connection is arranged on an outer surface of the support extending from a proximal end of the support in a distal direction such that the electrical connection is arranged at least in part between the support and the handle assembly.

19 Claims, 3 Drawing Sheets

ENDOSCOPE

CROSS-REFERENCE TO RELATED APPLICATION

The present application is based upon and claims the benefit of priority from U.S. Provisional Application No. 63/421,653 filed on Nov. 2, 2022, the entire contents of which is incorporated herein by reference.

BACKGROUND

Field

The present disclosure relates to endoscopes. More specifically, the present relates to endoscopes with a shaft assembly and a handle assembly, wherein the shaft assembly comprises a fiber tube, an outer shaft tube arranged around the fiber tube and a generally tubular support element proximally extending from the outer shaft tube; wherein the handle assembly is arranged generally around the support element; and an electrical connection element extending from a proximal end of the support element in a distal direction.

Prior Art

Endoscopes have long been used in medicine to perform examinations and treatments within body cavities of human patients and animals. For this purpose, endoscopes usually comprise an elongated shaft with an image recording device mounted at its distal tip which is directed to the location of interest during operation of the endoscope.

Endoscopes for visual inspection generally comprise a shaft assembly with a fiber tube and an outer shaft tube surrounding the fiber tube. A bundle of optical fibers is typically arranged between the fiber tube and the outer shaft tube in order to guide illumination light to the distal tip of the shaft.

Both the fiber tube and the outer shaft tube are coupled at or near their proximal ends through a support element which ensures a structural support between these tubes and acts as a guide for electrical connecting elements and optical fibers which pass between a proximal end of the endoscope and its distal tip. Furthermore, the endoscope can be surrounded by a handle assembly in the area of the support element with the handle assembly comprising an operating element. Both the handle assembly and the operating element serve medical personnel to manipulate the endoscope and activate or deactivate operational features. Electrical connecting elements of the operating element pass through the support element as well and towards a proximal direction of the endoscope.

However, known support elements have shown several drawbacks for the operation and the manufacturing of an endoscope.

On the one hand, guiding optical fibers or electrical connection elements through the support element requires openings in the structure.

After being used with a patient, an endoscope needs to be reprocessed before it can be used again with another patient. During reprocessing, the endoscope is subjected to chemicals, water, and steam at high temperatures and pressures, so that the endoscope needs to be sealed for protecting delicate optical and electronic components. Openings, however, present weak points in the sealing of the endoscope against an ingress of liquids.

On the other hand, an electrical connection to the operating element is sometimes established by use of flexible printed circuit boards guided through the opening. The connection of the flexible circuit board to electrical cables for a connection to external supply devices has to be established by soldering, which presents difficulties during manufacturing of such an endoscope, as the soldering has to take place in a limited space after assembling the shaft assembly. Furthermore, optical fibers from the distal tip of the endoscope have to be pulled through the support element, which poses a risk of breaking the fibers in the process.

Besides this, the support element accounts for a considerable share of weight and takes up space which, in turn, limits the possibilities for integrating additional electronic components into the endoscope.

Some attempts to improve the design of endoscopes have been made as to include an electrically conductive lead through the structure of the support element disclosed in German utility model DE 20 2022 103 092 U1.

SUMMARY

An object of the present disclosure is to provide an endoscope which is improved with respect to the above mentioned problems.

The present disclosure provides an endoscope with a shaft assembly and a handle assembly, wherein the shaft assembly comprises a fiber tube, an outer shaft tube arranged around the fiber tube and a generally tubular support element proximally extending from the outer shaft tube; wherein the handle assembly is arranged generally around the support element, and an electrical connection element is arranged on an outer surface of the support element extending from a proximal end of the support element in a distal direction, so that the electrical connection element is arranged at least in part between the support element and the handle assembly.

Such support element does not have any openings through which electrical connection elements are guided and can pose a reduced threat to the endoscope to suffer damage from an ingress of liquids or vapors in the space between the handle assembly and the support element. Furthermore, without an opening, sensitive internal components, e.g., optical fibers or an image recording device, are not directly exposed to contamination or corrosion.

In this document and as generally accepted in the art, a distal direction denominates the direction along the device towards the tip of the shaft of the endoscope, while a proximal direction points towards the user or the supply connections of the endoscope. Thus, the electrical connection element facilitates establishing an electrical contact to the space between the support element and the handle assembly from the proximal portion of the support element. During assembly of the endoscope, the proximal end of the support element is—in contrast to the space between the support element and the handle assembly—easy to reach and allows for simplified contacting.

While there is one electrical connection element mentioned, the disclosure is not limited thereto. Instead, an embodiment comprising a plurality of electrical connection elements arranged on the outer surface of the support element is covered by the disclosure as well.

The handle assembly can allow the user to manipulate the endoscope. It can contain one or multiple handle sections to control insertion depth, angle and orientation of certain parts of the shaft. Additionally, it can also contain operating elements which allow the user to control further functionalities. The handle assembly is typically arranged at the connection between the elongated shaft intended for insertion into the body cavity and the supply infrastructure as e.g., cables or tubes of electrical wires and optical fibers. At this location, the wires and fibers have to be directed into their appropriate intermediate space between the tubes or within the handle assembly, which can be achieved by the electrical connection element arranged on the support element.

In an embodiment, the support element can be injection-molded. This configuration can allow for a complex component incorporating a plurality of geometrical requirements to be manufactured in a comparably easy process while taking advantage of the availability of materials which are light of weight.

According to an embodiment of the disclosure, the support element including the electrical connection element can be manufactured as a molded interconnect device (MID). An MID is understood to be an injection-molded component with electronic circuits applied on its surface. The electrical connection element can in this case be structured on the surface of the previously molded MID. A configuration according to this embodiment can enable the manufacturing of support elements with contacting points at axially and radially defined positions to contact e.g., proximally arranged cables or contacts for actuation elements arranged at the handle assembly. Such a component with an integrated electrically conductive trace as electrical connection can retain its dimensions created in the injection-molding process. The electrically conductive trace does not cause any irregularities in the surface so that common means of sealing, such as O-rings, can be applied. The interior of the endoscope can, thus, be completely sealed from the space between the handle assembly and the support element while at the same time an electrical connection between these two locations can be established.

The support element can be made from PEEK-LDS. This material can be composed of thermoplastic polyether ether ketone (PEEK) which can be doped with an electrically non-conductive metallic inorganic compound. PEEK has a wide range of applications in prior an endoscopes and is known to tolerate harsh environmental conditions during reprocessing. Including metallic particles can allow the application of MID processes to create electrically conductive traces on the surface of the injection-molded component.

The electrical connection element of the endoscope can be manufactured through a laser direct structuring (LDS) process on the surface of the support element. Following this process, electrically conductive traces can be created through illumination of the appropriate regions with laser light. Where laser light is incident on the doped MID part, metallic additives can be activated forming an electrically conductive trace.

In an embodiment of an endoscope according to the present disclosure, an electrical connector can be disposed at the proximal end of the support element wherein the electrical connector can be configured to enable an electrical connection to the electrical connection element. This embodiment can allow for a further simplification in the assembly process. Instead of soldering the electrical connection element to supply wires when the support element is already mounted, the connector can be attached to the support element beforehand. After assembly of the outer shaft assembly, one or more supply wires can then easily be plugged into the electrical connector and, by doing so, can establish an electrical connection to the electrical connection element. The electrical connector can comprise several connection contacts which can be electrically connected to different electrical connection elements. The electrical connector can take any form of a plug, socket, adaptor or the like. Alternatively, a plurality of connectors can be provided as well.

Furthermore, in the endoscope according to the disclosure, an optical fiber bundle can be arranged in the space between the fiber tube and the outer shaft tube of the shaft assembly and the optical fiber bundle can be guided proximally of the outer shaft tube along the support element or in an axially extending recess of the support element. Optical fibers can serve in an endoscope of such kind to guide illumination light to the distal tip from where it is emitted to provide improved visual conditions. Typically, the optical fibers can be arranged between the fiber tube and the outer shaft tube and, for that reason, the optical fibers need to be guided through the space between the fiber tube and the support element. A recess axially extending along the support element in which the fibers are guided can allow for a slim overall construction of the whole assembly.

The endoscope can further comprise a connection insert arranged at a proximal end of the support element, wherein the optical fiber bundle can be guided to the connection insert, and wherein the connection insert can be configured to provide a connection for coupling illumination light into the optical fiber bundle. Comparable to the electrical connector mentioned above, an optical connection to the optical fiber bundle can be made at the proximal end of the support element in a plug-like manner. By this configuration, assembly of the endoscope can be largely simplified, as an improved protection for the delicate optical fibers can be provided which, in known endoscopes, have to be pulled through the whole device undergoing stronger tension forces and being possibly bent. Reliability of the optical fibers in the endoscope can be thus improved. If both the connection insert and the electrical connector as described above are disposed on the support element, the whole shaft assembly can be pre-manufactured before proceeding to later manufacturing steps, facilitating the assembly even further.

According to an embodiment of an endoscope according to this disclosure, a gap between the support element and the fiber shaft at a proximal end of the support element can be sealed. The gap can be sealed by a molding process or by soldering. Accordingly, the interior of the shaft assembly can be protected against an ingress of humidity or contaminants, providing an improved protection of the fibers.

The outer surface of the support element can comprise at least one of a protrusion or a recess configured to engage with complementary features of the handle assembly, in order to prevent the handle assembly from moving axially with respect to the support element. During manufacturing, the shaft can be inserted through the generally rotationally symmetric handle assembly until the protrusion or the recess or a combination interlock, e.g., through a clipping mechanism, with the handle assembly. The recess or protrusion can be positioned on the support element such that they are not in the path of the electrical connection element. If the electrical connection element is configured as conductive trace of an MID component, however, it can as well run through a recess or over a protrusion.

Moreover, in an endoscope according to the present disclosure, an operating element can be arranged on the handle assembly and the electrical connection element can be configured to form an electrical connection with the operating element. The operating element can be one or more buttons or switches of any kind which can allow the user of the endoscope to control functionalities of the endoscope or the surgical system in which it is used, such as illumination, image recording, application of energy or fluids and others. Two or more operating elements can as well be disposed on the handle assembly. In this case, different electrical connection elements can form electrical connections to different operating elements. The operating elements can comprise electrical contacts on the inside of the handle assembly which can be in line with contact areas formed by an MID process when the handle assembly is clipped to the support element. Via the electrical connector, a connection can be established to the operating elements.

In addition, according to the disclosure, the handle assembly can comprise a first handle section being rotationally fixed to the support element and/or the outer shaft tube, and a second handle section being rotatable around the support element. Rotating both handle sections relative to each other can provide additional means to manipulate the endoscope. In this configuration, the operating elements can be placed on the first handle section so that no means for providing a rotatable electrical connection element is needed.

In an embodiment of an endoscope according to the disclosure, the endoscope can furthermore comprise an inner shaft tube rotatably arranged in the fiber tube. An optical assembly can be arranged within the inner shaft tube. The optical assembly can comprise a digital image sensor which can, through rotation, be oriented to provide a picture in a preferred viewing direction. Alternatively, the optical assembly can comprise optical components such as prisms, mirrors, and lenses which, again, can be rotated to provide a lateral view as needed.

The second handle section can be rotationally coupled to the inner shaft tube. Thus, the viewing direction of the optical assembly can be manipulated by the user via the handle assembly. The rotational coupling can be achieved through a magnetic coupling.

The disclosure further provides a method for manufacturing an endoscope.

BRIEF DESCRIPTION OF THE DRAWINGS

An embodiment of the disclosure is explained in more detail below by means of exemplary visualizations. The embodiment example shown is only intended to contribute to a better understanding of the invention without limiting it. In this connection, the drawing is not to scale in order to permit a better representation of the elements relevant to the invention.

In the drawings.

DETAILED DESCRIPTION

Figure 1:
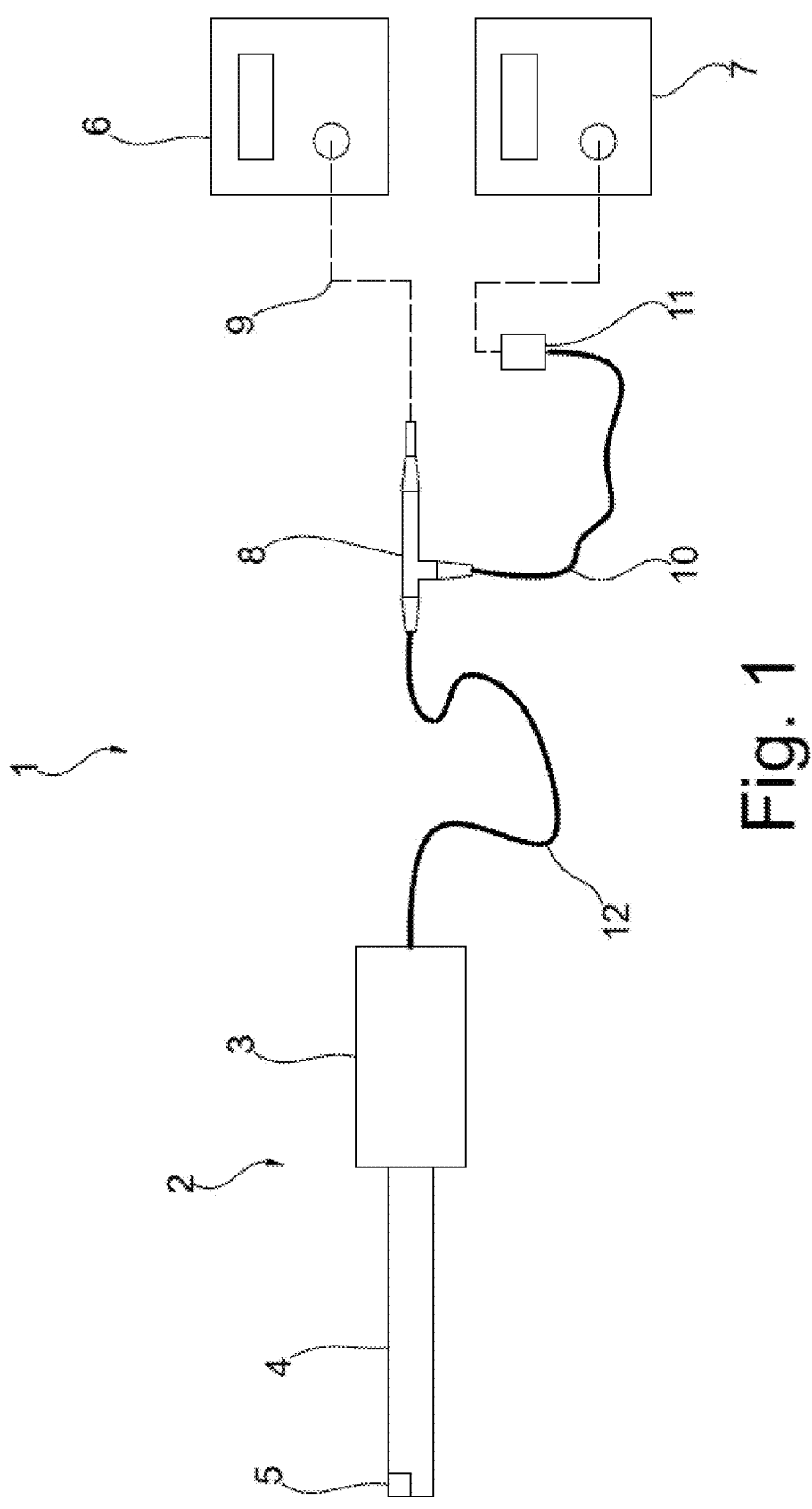
FIG. 1 illustrates an endoscopic system.

FIG. 1 is an illustration of an endoscopic system 1 in which an endoscope 2 according to the disclosure can be operated. The endoscope 2 comprises a main body 3 and an elongated shaft 4. The main body 3 can include a housing protecting components against environmental influences and a handle assembly used to manipulate the endoscope 2 during use. During a medical intervention, the elongated shaft 4 is introduced into a body cavity of a patient in order to allow the physician to visually evaluate an area of interest. For this purpose, an optical assembly 5 is disposed at the distal tip of the shaft 4 either recording electronic images using an image sensor or optically guiding a picture via mirrors and lenses towards a proximal part of the device.

During a procedure, the exemplary endoscope 2 needs to be supplied with electrical energy and illumination light while the recorded image is transmitted to an image processing device. Illumination light is generated e.g., by a light source 6, which can include a laser light source, while a camera control unit 7 provides electrical energy and receives the recorded images and commands from the user. However, the disclosure is not limited thereto, and other substances and forms of energy can as well be provided to or received by the endoscope 2.

Connection between the endoscope 2 and supply devices including the light source 6 and the camera control unit 7 is established via a coupling unit 8, which can be plugged into a receiving socket of the light source 6 as indicated by the dashed line 9. For establishing an electrical connection, a cable 10 can be connected via a plug 11 to the camera control unit 7. Within the coupling unit 8, optical fibers and wires for electrical communication are routed into a common cable 12 leading to the endoscope 2.

Figure 2:
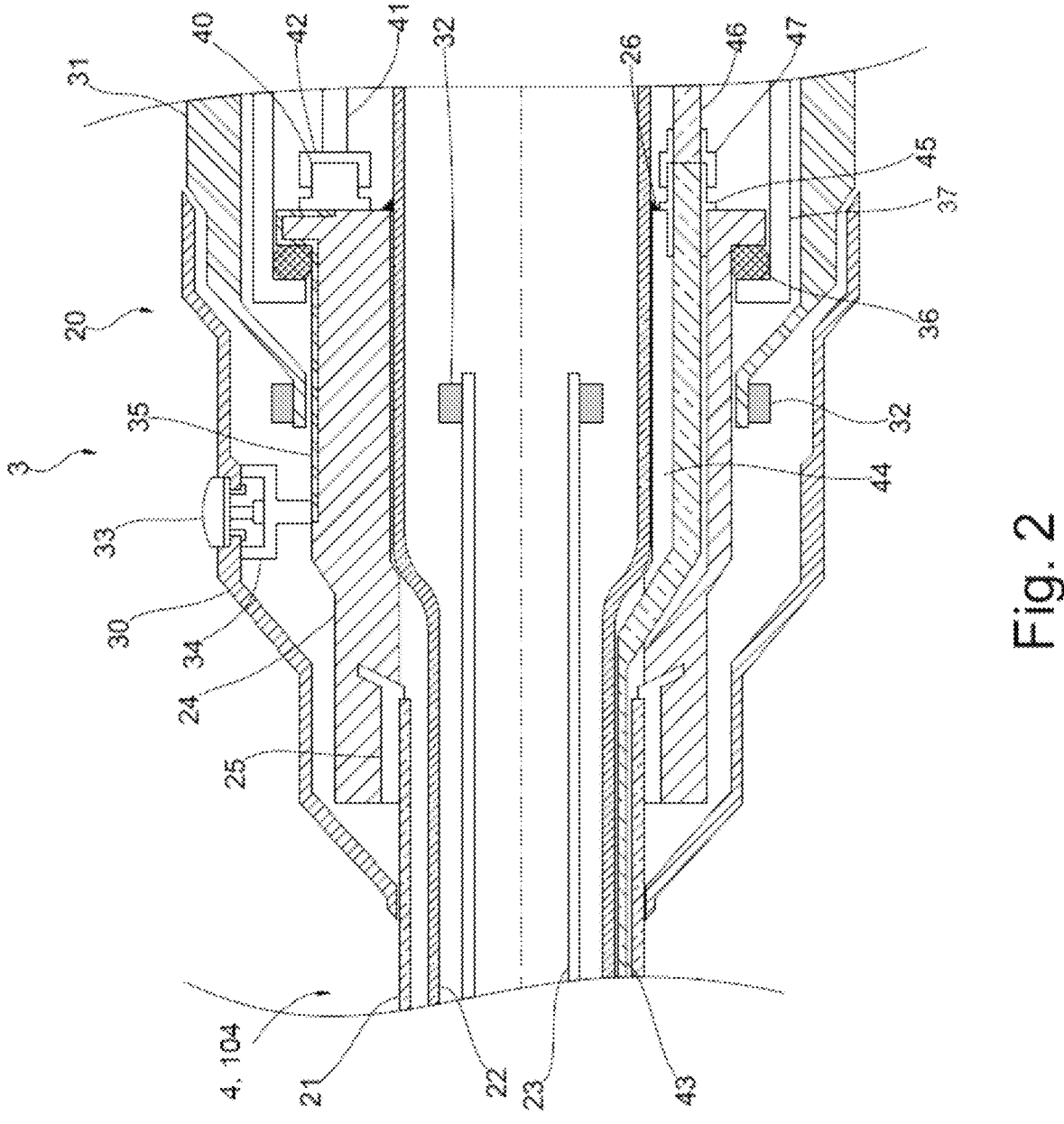
FIG. 2 illustrates an endoscope according to the disclosure.

FIG. 2 shows a cross-section through a part of an endoscope according to the disclosure. Within the main body 3, electrical and optical connections established with the corresponding supply devices through the common cable 12 are continued in such a way that the energy carrier reaches its respective target locations. In the endoscope according to this disclosure, an electrical connection is provided to a distal part of handle assembly 20 while illumination light is guided to the distal tip of the endoscope 3. Further connections can be provided in the endoscope to supply an optical assembly, heating elements or the like. However, since supply of such components is not relevant to the present disclosure, they are omitted from this illustration for clarity. Nonetheless, such components can also be used with such an endoscope according to the disclosure.

The shaft 4 of the endoscope 2 is formed as shaft assembly 104 comprising an outer shaft tube 21 and a fiber tube 22. The illustrated endoscope 2 also includes an inner shaft tube 23. The inner shaft tube can house an optical assembly (not shown in FIG. 2), such as the optical assembly 5, and can be rotatably arranged within the fiber tube 22. The outer shaft tube 21 and the fiber tube 22 are rotationally fixed to each other via a support element 24. The support element 24 comprises a receiving member 25 receiving the outer shaft tube 21. In the example, the receiving member 25 is molded into the support element 24, but can also be bonded or otherwise secured therein. The outer shaft tube 21 can be welded, soldered, or otherwise fixed to the receiving member 25. The support element 24 is secured to the fiber tube 22 by a solder joint 26, but can also fixed using an adhesive or a molding process, with all approaches sealing a remaining gap between the support member 24 and the fiber tube 22. Accordingly, a space between the outer shaft tube 21 and the fiber tube 22 is sealed off by the support body 24 against ingress of liquid, vapor, or contaminants.

The handle assembly 20 is disposed generally around the support element 24 and comprises, in the shown embodiment, a first handle section 30 and a second handle section 31. The first handle section 30 is rotationally fixed relative to the shaft assembly 104 and the support element 24, and the second handle section 31 can be rotated around the support element 24, the first handle section 30, and the shaft assembly 104. In the shown embodiment, the second handle section 31 is rotationally coupled to the inner shaft tube 23 via a magnetic coupling 32.

The first handle section 30 comprises an operating element 33 in the form of a push button switch. In other embodiments, the endoscope can also comprise more than one operating element, e.g., three push button switches. Instead of push button switches, other kinds of buttons, switches, knobs, sliders and the like can be used to allow the user controlling operating functionalities of the endoscope 2.

The operating element 33 visible to the outside is mechanically in contact with an underlying contact switch mounted on a contact bridge 34. So that the signal from the contact switch can be routed to the outside, the contact bridge 34 forms an electrical contact with an electrical connection element 35, which extends from a proximal end of the support element 24 in a distal direction on an outer surface of the support element 24. Thereby, the electrical connection 35 element runs at least in part in the space between the support element 24 and the handle assembly 20.

In the shown embodiment, the electrical connection element 35 is formed as an electrically conductive trace within the surface of the support element 24. Since the support element 24 is manufactured here by an injection-molding process, the support element 24 together with the electrical connection element 35 belongs to the category of molded interconnect devices (MID). The electrical connection element 35 is formed in the surface of the support element 24 after the injection-molding process has been completed. Various processes are available for this purpose, e.g., laser direct structuring, where laser light incident on the molded part activates metallic additives embedded in the injection-molding material. A suitable material used in this example is PEEK-LDS which is composed of polyether ether ketone (PEEK) doped with metallic additives.

By using electrical connection elements such as the electrical connection element 35, sealing of the interior of the endoscope 2 can be achieved by a conventional seal, such as an O-ring 36 between the support element 24 and a housing element 37. In addition, further seals can be provided in locations such as between the first and the second handle sections 30, 31, between the first handle section 30 and the outer shaft tube 21, between the second handle section 31 and the housing element 37, and others. Such further seals are not illustrated here for reasons of simplicity.

Within the main body 3, an electrical connection is established between the electrical connection element 35 and corresponding wires in the common cable 12. For this purpose, an electrical connector 40 is provided at the proximal end of the support element 24 through which an electrical connection can be made to the electrical connection element 35. The electrical connector 40 can as well be placed in proximity to the proximal end of the support element 24. The electrical connector 40 is placed within the main body 3 of the endoscope 2 in such a manner that it is sufficiently sealed against an ingress of liquids and contaminants. During manufacturing of the endoscope 3, a connection cable 41 leading to the common cable 12, which is provided with a cable connector 42, can be plugged directly into the electrical connector 40, which is provided as a socket in this embodiment. As an alternative to the illustrated embodiment, different configurations of plugs, sockets, connectors, adaptors, and the like can also be used. A plurality of such connectors can also be provided.

Within the shaft assembly 104, between the outer shaft tube 21 and the fiber tube 22 an optical fiber bundle 43 is provided for guiding illumination light to the distal tip of the shaft 4. In a proximal direction, after leaving the space between the shaft tube 21 and the fiber tube 22, the optical fiber bundle 43 is guided along the inner surface of the support element 24 in and along an axially extending recess 44 of the support element 24 towards the proximal end of the support element 24.

The optical fiber bundle 43 terminates in a connection insert 45 inserted in a proximal end of the recess 44. At the connection insert, 45 a supply bundle of fibers 46 leading to the common cable 12, which is provided with a corresponding optical connector 47, can be attached in order to allow coupling of illumination light into the optical fiber bundle 43.

The endoscope 2 as described herein, provided with a support element 24 comprising an electrical connection element 35 and a connection insert 45, can be assembled particularly easy. The support element 24, the outer shaft tube 21, the fiber tube 22 and the optical fiber bundle 43 can be manufactured as one sub-assembly before mounting further components as e.g., the inner shaft tube 23.

A procedure for mounting of the endoscope 2 is described below. In a first step, the shaft 4 is mounted using the outer shaft tube, the fiber tube 22, the fiber bundle 43, and the support element 24. In a second step, the connection cable 41 and the bundle of fibers 46 are connected to the support element 24, using the connector 40 and the connection insert 45. In a next step, the O-ring 36 and the housing element 37 are slid over the shaft 4 from the distal direction, so that a distal flange of the housing element 37 and a proximal flange of the support element 24 abut the O-ring 36. Support body 24 and housing element 37 can be secured relative to each other by a nut screw (not shown), which can be screwed onto an external thread (not shown) on the support body 24. The thread can have one or more axial grooves (not shown) through which the connection element 35 can be routed.

After securing the housing element 37, the second handle section 31 can be pushed over the housing element from the distal side, before the contact bridge 34 is attached to the connection element 35, e.g., by soldering. In a final step, the first handle section 30 is pushed over and fixed to the shaft 4 so that an opening in the first handle section exposes the contact bridge 34, and the operating element 33 is inserted into the opening.

Figure 3:
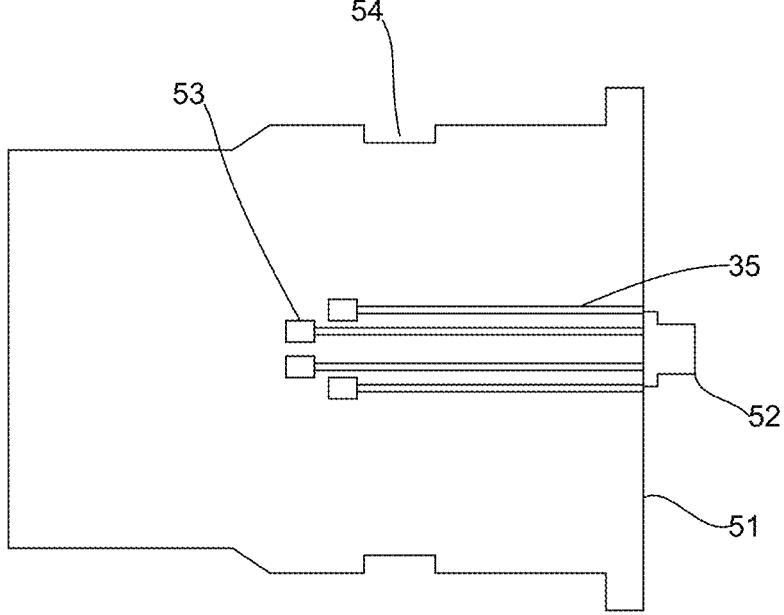
FIG. 3 illustrates a support element for an endoscope according to the disclosure.

FIG. 3 illustrates a support element 51 according to an embodiment of the disclosure. The support element 51 is similar to the support element 24. For that reason, only differences and additional features are addressed in the following. Again, the support element 51 comprises an electrical connector 52. However, in this embodiment a multitude of electrical connection elements 35 is provided each of which terminates in distal direction in a respective contacting pad 53. The contacting pads 53 can account for small manufacturing deviations when sliding the handle assembly, e.g., the handle assembly 20 including the contact bridge 34, over the support element 51.

Additionally, the support element 51 optionally comprises recesses 54. These recesses are configured to engage with complementary features of the handle assembly 20 in order to prevent the handle assembly 20 from moving axially. During manufacturing, the handle assembly 20 can be moved over the shaft assembly 104 including the support element 51 until the recesses 54 interlock, e.g., through a clipping mechanism, with the handle assembly 20. Alternatively, instead of recesses 54, protrusions can be provided as well.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that can fall within the scope of the appended claims.

What is claimed is:

1. An endoscope comprising:
a shaft assembly; and
a handle assembly;
wherein the shaft assembly comprises:
    a fiber tube;
    an outer shaft tube arranged around the fiber tube; and
    a support proximally extending from the outer shaft tube;
wherein the handle assembly is arranged around the support, and
an electrical connection is arranged on an outer surface of the support extending from a proximal end of the support in a distal direction such that the electrical connection is arranged at least in part between the support and the handle assembly.

2. The endoscope according to claim 1, wherein the support is injection molded.

3. The endoscope according to claim 1, wherein the support including the electrical connection is manufactured as a molded interconnect device.

4. The endoscope according to claim 1, wherein the support is made from PEEK-LDS.

5. The endoscope according to claim 3, wherein the electrical connection is manufactured through a laser direct structuring process on the surface of the support.

6. The endoscope according to claim 1, wherein an electrical connector is disposed at the proximal end of the support and the electrical connector is connected to the electrical connection.

7. The endoscope according to claim 1, further comprising an optical fiber bundle arranged between the fiber tube and the outer shaft tube of the shaft assembly, and the optical fiber bundle extends proximally of the outer shaft tube one of along the support or in an axially extending recess of the support.

8. The endoscope according to claim 7, further comprising a connection insert arranged at a proximal end of the support, wherein the connection insert is connected to the optical fiber bundle and the connection insert is configured to provide a connection for coupling illumination light into the optical fiber bundle.

9. The endoscope according to claim 1, further comprising a seal provided in a gap between the support and the fiber tube at a proximal end of the support.

10. The endoscope according to claim 9, wherein the seal is provided by a molding process or by soldering.

11. The endoscope according to claim 1, wherein the outer surface of the support comprises at least one of a protrusion or a recess configured to engage with a complementary feature of the handle assembly to prevent the handle assembly from moving axially relative to the support.

12. The endoscope according to claim 1, further comprising a switch arranged on the handle assembly and the electrical connection is configured to form an electrical connection with the switch.

13. The endoscope according to claim 12, wherein the switch comprises one or more button switches.

14. The endoscope according to claim 1, wherein the handle assembly comprises:
a first handle rotationally fixed to one or more of the support and the outer shaft tube, and
a second handle being rotatable around the support.

15. The endoscope according to claim 1, further comprising an inner shaft tube rotatably arranged in the fiber tube.

16. The endoscope according to claim 15, wherein an optical assembly is arranged within the inner shaft tube.

17. The endoscope according to claim 15, wherein the handle assembly comprises a first handle rotationally fixed to one or more of the support and the outer shaft tube, and a second handle being rotatable around the support, wherein the second handle is rotationally coupled to the inner shaft tube.

18. The endoscope according to claim 1, wherein the support has a cross-section in a direction perpendicular to a longitudinal axis of the fiber tube that is at least partially tubular.

19. The endoscope according to claim 1, wherein the electrical connection is a trace of conductive material arranged on the outer surface of the support.

\* \* \* \* \*